United States Patent [19]
Kimura et al.

[11] Patent Number: 5,810,796
[45] Date of Patent: Sep. 22, 1998

[54] ABSORBENT ARTICLE

[75] Inventors: Mayumi Kimura; Yayoi Fukuhara; Mitsugu Hamajima; Minoru Nakanishi, all of Tochigi-ken, Japan

[73] Assignee: KAO Corporation, Tokyo, Japan

[21] Appl. No.: 779,078

[22] Filed: Jan. 8, 1997

[30] Foreign Application Priority Data

Jan. 10, 1996 [JP] Japan ..................... 8-002054

[51] Int. Cl.⁶ ............... A61F 13/15; A61F 13/20
[52] U.S. Cl. ........................... 604/365; 604/368
[58] Field of Search .................. 604/365, 378, 604/379, 380, 385.1, 387, 367–375

[56] References Cited

U.S. PATENT DOCUMENTS

| | | | |
|---|---|---|---|
| 4,798,601 | 1/1989 | Shirose et al. | 604/368 |
| 5,248,309 | 9/1993 | Serbiak et al. | 604/378 |
| 5,460,623 | 10/1995 | Emenaker et al. | 604/368 |
| 5,509,914 | 4/1996 | Osborn, III | 604/368 |
| 5,578,025 | 11/1996 | May | 604/368 |
| 5,607,414 | 3/1997 | Richards et al. | 604/368 |

*Primary Examiner*—Mark O. Polutta
*Assistant Examiner*—Ki Yong O
*Attorney, Agent, or Firm*—Birch, Stewart, Kolasch & Birch, LLP

[57] ABSTRACT

An absorbent article which comprises at least a liquid retentive absorbent member and a liquid impermeable anti-leakage layer, wherein the liquid retentive absorbent member has a bending stiffness of 0.05 to 1.0 gf·cm along its lateral direction and a compressive modulus of $2 \times 10^6$ to $1 \times 10^8$ dyne/cm$^2$ along its lateral direction.

9 Claims, 2 Drawing Sheets

ABSORBENT ARTICLE

BACKGROUND OF THE INVENTION

1. Field of the Invention

This invention relates to an absorbent article, and more particularly to an absorbent article that is thin and soft, hardly undergoes deformation during use, and feels very comfortable while being worn.

2. Description of the Related Art

An absorbent member which has been used in absorbent articles, such as sanitary napkins, generally comprises combination of pulp or compressed pulp with a superabsorbent polymer. Such an absorbent member has high absorptivity but, on the other hand, gives a feeling foreign to a wearer because of its large thickness and is not deemed to be comfortable during use. In addition, a conventional sanitary napkin tends to deform, which may cause reduction in absorptivity, or shift out of position with the wearer's movement.

In order to eliminate these drawbacks of conventional sanitary napkins, Japanese Patent Application Laid-Open 2-11137 which corresponds to U.S. Pat. Nos. 5,383,869 and 5,509,914 proposes a sanitary napkin which is designed with weight put on its flex resistance (equivalent to "bending stiffness" described herein after) so as to be a good fit to the wearer's body. More specifically, the application discloses a sanitary napkin having a test absorption of 8.0 g or higher, a total absorption of 20.0 g or higher, and a flex resistance of less than 300.0 g.

The sanitary napkin disclosed in the above application feels less foreign to a wearer owing to its low flex resistance but, in turn, easily undergoes greater deformation, which results in insufficient liquid absorption or causes back flow or leakage of absorbed liquid. In addition, above patent is concerned with softness of the sanitary napkin by specifying the flex resistance, but is no concern with the prevention of the deformation of the sanitary napkin.

SUMMARY OF THE INVENTION

Accordingly, an object of the present invention is to provide an absorbent article which is difficult to deform and feels very comfortable while being worn.

The inventors of the present invention have extensively studied in order to accomplish the above object and have found that comfort and deformation of an absorbent article are greatly influenced by not only its bending stiffness but also by its compressive modulus. As a result of further investigation, the inventors have found that an absorbent article which is difficult to deform and is comfortable during wear can be obtained by using an absorbent member having a high compressive modulus and a low bending stiffness, particularly along its lateral direction.

Based on this finding, the above object is accomplished by an absorbent article which comprises a liquid retentive absorbent member and a liquid impermeable antileakage layer, wherein the liquid retentive absorbent member has a bending stiffness of 0.05 to 1.0 gf·cm along its lateral direction and a compressive modulus of $2 \times 10^6$ to $1 \times 10^8$ dyne/cm$^2$ along its lateral direction.

The absorbent article of the present invention is suitable for use as a sanitary napkin, a hygiene pad, a disposable diaper, a medical pad, a nursing breast pad, etc. It is especially suitable for use as a sanitary napkin.

According to the present invention, use of an absorbent member having a high compressive modulus and a low bending stiffness in its lateral direction provides a comfortable absorbent article which is difficult to deform, feels less foreign to a wearer's body, and causes little leakage.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus are not limitative of the present invention, and wherein:

DETAILED DESCRIPTION OF THE INVENTION

Figure 1:
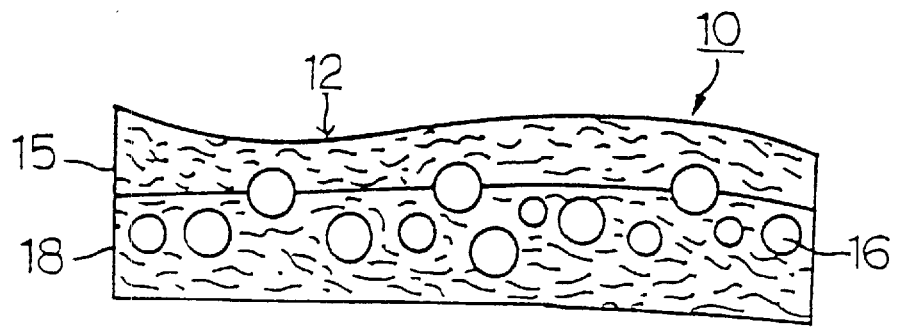
FIG. 1 is a schematic sectional view of the absorbent sheet which is preferably used in the absorbent article of the present invention.

As described above, the present invention provides an absorbent article which is difficult to deform and is more comfortable during wear and having a certain range of bending stiffness and a compressive modulus, both in the lateral direction of an absorbent member. More particularly, it is important in the present invention that the absorbent member be designed to have reduced bending stiffness along its lateral direction and an increased compressive modulus along its lateral direction. The bending stiffness along its lateral direction as used herein means a stiffness measured by bending the absorbent article parallel to the longitudinal direction of the absorbent article. The compressive modulus along its lateral direction as used herein is measured by the following manner: first, the absorbent member is made into a cylindrical shape with the longitudinal direction of the absorbent member as a circumferential direction of the cylinder, and second, the cylinder is compressed in its height direction. In more detail, the absorbent member in the absorbent article of the present invention has a bending stiffness of 0.05 to 1.0 gf·cm in its lateral direction and a compressive modulus of $2 \times 10^6$ to $1 \times 10^8$ dyne/cm$^2$ in its lateral direction. If the bending stiffness is less than 0.05 gf·cm, the absorbent article is very soft as a whole and lacks stiffness so that it will not be fixed to, e.g., panties smoothly, and will deform at the very start of use. If the bending stiffness exceeds 1.0 gf·cm, the absorbent article gives a foreign a feeling to a wearer. If the compressive modulus is less than $2 \times 10^6$ dyne/cm$^2$, the absorbent article is apt to deform. If it exceeds $1 \times 10^8$ dyne/cm$^2$, the absorbent member has high stiffness to give a foreign feeling and, when a stress is applied externally, is hardly deforms so that the absorbent article is apt to be shifted out of position. The absorbent member preferably has a bending stiffness of 0.1 to 0.7 gf·cm, more preferably 0.3 to 0.5 gf·cm in its lateral direction, and a compressive modulus of $5 \times 10^6$ to $0.5 \times 10^8$ dyne/cm$^2$, more preferably $6 \times 10^6$ to $0.3 \times 10^8$ dyne/cm$^2$ in its lateral direction.

The details of measurement of the bending stiffness and compressive modulus will be described in Examples hereinafter.

Thus, one of the features of the present invention resides in a reduced bending stiffness and an increased compressive modulus of an absorbent member, which are seemingly conflicting with each other, to provide an absorbent article comprising an absorbent member possessing these characteristics.

The liquid retentive absorbent member in the absorbent article of the invention preferably has a total basis weight of 21 to 500 g/m$^2$, still preferably 30 to 300 g/m$^2$, particularly preferably 50 to 200 g/m$^2$.

In order for the liquid retentive absorbent member to have a reduced and stabilized bending stiffness, the thickness of the absorbent member under a load of 2.5 g/cm$^2$ is preferably 0.3 to 3 mm, still preferably 0.3 to 1.5 mm, and particularly preferably 0.5 to 1.2 mm.

It is also preferable for the liquid retentive absorbent member to be shaped in accordance with the crotch of a wearer. For example, the absorbent member is preferably shaped so that the portion corresponding to the upper inner thighs is narrowed (that is, shaped like a so-called sandglass) or curved to form a boat shape.

Any absorbent member can be applied to absorbent articles of the present invention with no particular limitation as far as the bending stiffness and the compressive modulus of the absorbent member fall within the above-described respective ranges.

In order to reduce the bending stiffness of an absorbent member, it is important to reduce the thickness of the absorbent member by increasing the absorption ability of the superabsorbent polymer used in the absorbent member, or alternatively, by increasing the degree of dispersing of the superabsorbent polymer in the absorbent member, thereby to improve the absorption efficiency and to reduce the amount of materials used. On the other hand, in order to increase the compressive modulus, it is important to incorporate into the absorbent member an absorbent sheet containing thermally-fusible bonding fibers which have been three-dimensionally bonded to each other.

The absorbent member having a reduced bending stiffness and an increased compressive modulus used in the present invention is preferably one containing at least a superabsorbent polymer and an absorbent sheet. The absorbent sheet is preferably made up of at least hydrophilic fibers and thermally-fusible bonding fibers. The hydrophilic fibers and the thermally-fusible bonding fibers can be those used in a preferred absorbent sheet hereinafter described in detail. The absorbent member containing the superabsorbent polymer, hydrophilic fibers and thermally-fusible bonding fibers has, for example, a structure in which the hydrophilic fibers form a three-dimensional network by the aid of the thermally-fusible bonding fibers, with the superabsorbent polymer dispersed and fixed within the network.

A preferred example of the absorbent member used in the absorbent article of the present invention is an absorbent sheet containing at least a superabsorbent polymer. Such an absorbent sheet will be explained below by referring to the accompanying drawings.

Figure 2:
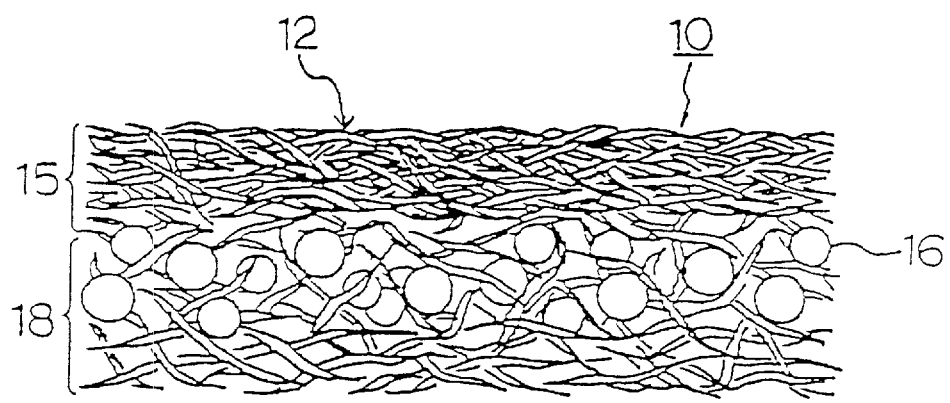
FIG. 2 is a schematic cross-sectional view of an absorbent sheet which is particularly preferably used in the absorbent article of the present invention.

FIG. 1 is a schematic sectional view of an absorbent sheet which is preferably used in the absorbent article of the present invention. FIG. 2 is a schematic cross-sectional view of an absorbent sheet which is particularly preferably used in the absorbent article of the present invention.

It should be noted that the absorbent sheets shown in FIG. 1 and FIG. 2 are only preferable examples used as the absorbent member of the absorbent article of the present invention and the absorbent member is not limited to the sheet shown in FIG. 1 and 2.

As shown in FIGS. 1 and 2, an absorbent sheet 10, which is preferably used as an absorbent member in the absorbent article of the present invention, contains at least a superabsorbent polymer 16. The absorbent sheet 10 comprises a fiber aggregate layer 15 and a fiber web layer 18, and the fiber aggregate layer 15 and the fiber web layer 18 forming a unitary body (The fiber aggregate layer hereinafter simply referred to as "fiber aggregate" and the fiber web layer hereinafter simply referred to as "fiber web").

The fiber aggregate 15 has an absorbent surface 12 and does not contain the superabsorbent polymer 16 on the side of the absorbent surface.

The fiber web 18 comprises at least hydrophilic fibers and thermally-fusible bonding fibers.

The superabsorbent polymer 16 is adhered to the fibers constituting the absorbent sheet 10 and is dispersed and fixed predominantly in the fiber web 18 and in the interface between the fiber web 18 and the fiber aggregate 15.

The absorbent sheet 10 shown in FIGS. 1 and 2 thus has an integral structure comprising the fiber aggregate 15 and the fiber web 18 and contains the superabsorbent polymer 16 in the inside thereof. Such a structure makes it possible to make the absorbent member extremely thin while containing the superabsorbent polymer 16 within the inside thereof, thereby achieving the above-described reduced bending stiffness. Since the portion of the fiber web 18 where the superabsorbent polymer 16 is contained has a three-dimensional structure bounded by thermally-fusible bonding fibers, the absorbent member can have an increased compressive modulus.

Owing to the above structure, the superabsorbent polymer 16 can be fixed in a large amount in the absorbent member and prevented from falling off, and liquid absorbed from the absorbent surface 12 can smoothly reach the superabsorbent polymer 16. Further, the superabsorbent polymer 16 having absorbed liquid can be prevented from causing gel blocking. Thus, there is easily obtained an absorbent article which is extremely thin and yet exhibits high absorption, hardly gives a foreign feeling, and hardly causes deformation and leakage.

In the absorbent sheet 10, the fiber aggregate 15 and the fiber web 18 are integrated into a unitary body through mechanical entanglement, hydrogen bonding (and with the aid of a reinforcing agent), thermal bonding, and the like between the fibers constituting the fiber aggregate 15 and the fibers constituting the fiber web 18. In particular, integration by thermal bonding is preferred in order to avoid reduction in compressive modulus after liquid absorption. An absorbent member using the absorbent sheet 10 has a structure utterly different from that of a conventional absorbent sheet in which a superabsorbent polymer is held in a layer between two distinctive, separate sheets of absorbent paper (i.e., the conventional absorbent sheet has a two-ply structure while the above-described absorbent sheet is a single sheet) and thus can be designed to have a very small thickness, reduced bending stiffness and increased compressive modulus.

The details of the hydrophilic fibers, thermally-fusible bonding fibers, superabsorbent polymer, and the like which constitute the absorbent sheet 10 will hereinafter be described.

Figure 3:
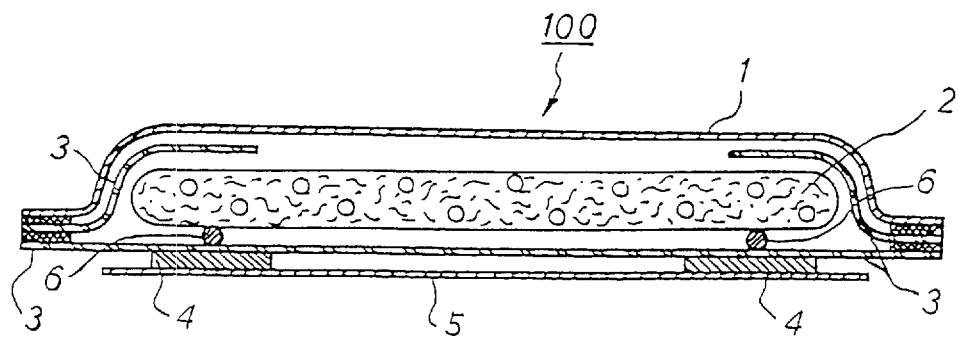
FIG. 3 is a transverse cross-sectional view of a sanitary napkin as a first embodiment of the absorbent article of the present invention.

Next, the absorbent article according to the present invention is explained by referring to the accompanying drawings. FIG. 3 is a transverse cross-section of a sanitary napkin as a first embodiment of the absorbent article of the present invention.

A sanitary napkin 100 shown in FIG. 3 has the above-mentioned preferred absorbent sheet as an absorbent member 2 and a liquid impermeable antileakage layer 3 which covers the longitudinal sides and the bottom of the absorbent member 2. The sanitary napkin 100 also has a liquid permeable surface layer 1 on the side to be brought into contact with the wearer's skin.

In more detail, the sanitary napkin 100 shown in FIG. 3 is shaped substantially in a rectangle and is designed to be worn with the surface layer 1 in contact with the skin and the antileakage layer 3 in contact with underwear. The surface layer 1 and the antileakage layer 3 are heat-sealed together at both sides and the front and rear edges of the sanitary napkin 100, and the heat-sealed areas are trimmed. The absorbent sheet as an absorbent member 2 is disposed with its upper layer on the side to be in contact with the wearer's skin. On the side of the absorbent article to be brought into contact with underwear are provided a pair of adhesive strips 4,4 in parallel with the longitudinal direction of the sanitary napkin. The adhesive strips 4,4 are protected by a release paper 5 before use. In FIG. 3, reference numeral 6 indicates joints at which the above-mentioned members are jointed together. Other undescribed particulars are the same as in conventional sanitary napkins.

The surface layer 1 preferably has a touch like underwear while exhibiting liquid permeability. Such a surface layer includes a perforated film obtained by making a number of perforations in a polyolefin film such as a polyethylene film, and a nonwoven fabric comprising polyethylene fibers, polypropylene fibers, polyester fibers or composite fibers thereof. The antileakage layer 3 is not particularly limited as far as it is impermeable to liquid. A antileakage layer having moisture permeability and an underwear-like touch are preferred. A moisture permeable and liquid impermeable antileakage layer can be obtained by, for example, melt-extruding a thermoplastic resin containing an organic or inorganic filler into a film through a T-die or a circular die and monoaxially or biaxially stretching the extruded film.

According to the above-described embodiment, because the absorbent member 2 is extremely thin, it has a reduced bending stiffness. Further, since the surface layer 1 does not enclose the absorbent member 2, the napkin itself has a reduced thickness. As a result, the sanitary napkin 100 according to this embodiment provides improved comfort to the wearer.

Figure 4:
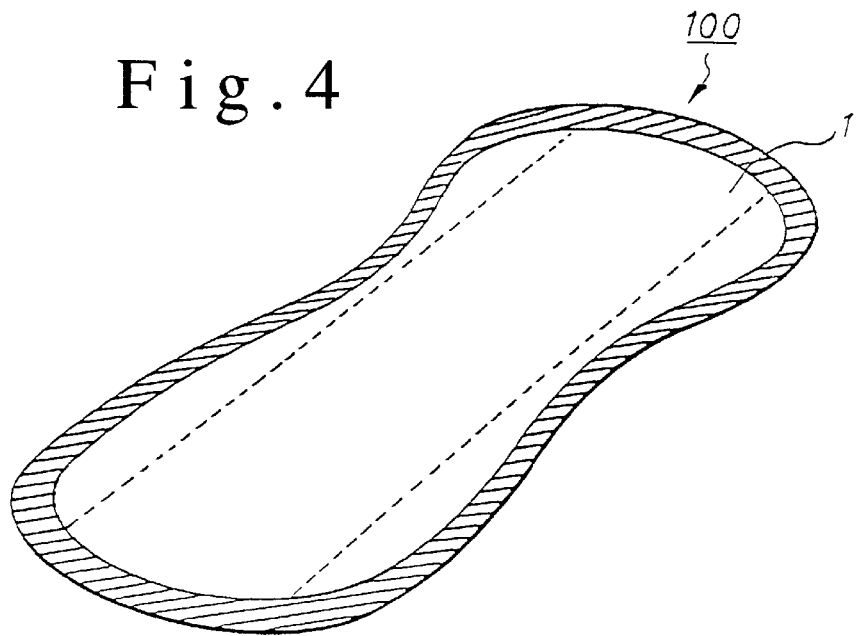
FIG. 4 is a perspective view of a sanitary napkin as a second embodiment of the absorbent article of the present invention.
Figure 5:
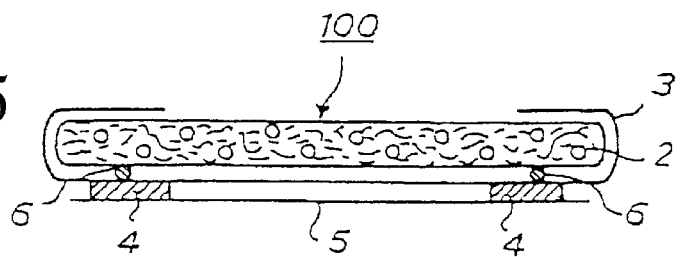
FIG. 5 is a transverse cross-sectional view of a sanitary napkin as a third embodiment of the absorbent article of the present invention (corresponding to FIG. 3).
Figure 6:
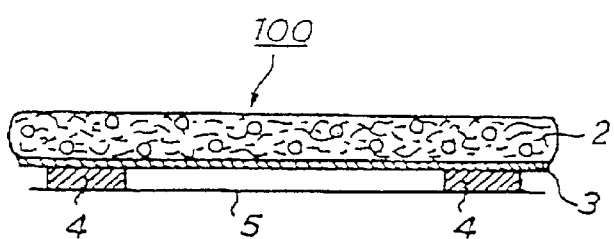
FIG. 6 is a transverse cross-sectional view of a sanitary napkin as a fourth embodiment of the absorbent article of the present invention (corresponding to FIG. 3).

Sanitary napkins 100 according a second to fourth embodiments of the absorbent article of the present invention are depicted in FIGS. 4 through 6.

FIG. 4 is a perspective view of a sanitary napkin as a second embodiment of the absorbent article of the present invention. FIG. 5 is a transverse cross-sectional view of a sanitary napkin as a third embodiment of the absorbent article of the present invention (corresponding to FIG. 3). FIG. 6 is a transverse cross-sectional view of a sanitary napkin as a fourth embodiment of the absorbent article of the present invention (corresponding to FIG. 3). While the particulars of the second to forth embodiments which are common to the first embodiment are not described, the corresponding explanation given to the first embodiment applies appropriately. The same reference numerals as used in FIG. 3 are used for the same members of FIGS. 4 to 6.

The sanitary napkin 100 shown in FIG. 4 has almost the same structure as in that of the first embodiment, except that the napkin (inclusive of the absorbent member) is shaped in accordance with the shape of a female crotch. Being so shaped, the sanitary napkin of this embodiment has an improved fit and is prevented from being deformed or shifted, giving improved comfort to a wearer while being worn.

The sanitary napkin shown in FIG. 5 has an absorbent member 2 and a antileakage layer 3, with the absorbent member 2 disposed on the side to come in contact with the skin of the wearer. The absorbent sheet as an absorbent member 2 is put with its fiber aggregate on the side to come in contact with the skin. In this case, the fiber aggregate is preferably made of a synthetic fiber (e.g., nonwoven fabric) rather than wood pulp (e.g., absorbent paper). A fiber aggregate made of synthetic fiber also feels less damp.

Having no surface layer, the sanitary napkin according to the above embodiment during wear is thin, thus having improved comfort during wear. Further, the sanitary napkin of this type can be produced through a simpler process at a lower cost because the number of constituent members is smaller. The absorbent article according to this embodiment is suitable not only as a sanitary napkin as shown in FIG. 5 but also in articles which are expected to absorb a little liquid, such as a nursing breast pad and a hygiene pad.

The sanitary napkin 100 shown in FIG. 6 comprises the above-described absorbent sheet as an absorbent member 2 and a liquid impermeable antileakage layer 3 directly bonded to the absorbent sheet. It is particularly preferable that the absorbent sheet be disposed with its fiber aggregate having an absorbent surface on the liquid absorbent side, and the liquid impermeable antileakage layer 3 be bonded to the side opposite the absorbent surface. In this case, too, the fiber aggregate is preferably made of a synthetic fiber (e.g., nonwoven fabric) rather than wood pulp (e.g., absorbent paper). A fiber aggregate made of synthetic fiber also feels less damp.

The sanitary napkin 100 according to this embodiment can have its thickness further reduced. In addition, the number of constituent members is still less. As a result, still further improved comfort is secured, and the sanitary napkin can be produced through a yet simpler process at a yet lower cost. The absorbent article according to this embodiment is suitable not only as a sanitary napkin as shown in FIG. 6 but also in articles which are expected to absorb a little liquid, such as a nursing breast pad and a hygiene pad.

The fiber web, fiber aggregate, and superabsorbent polymer constituting the above-described absorbent sheet which is preferably used as an absorbent member of the absorbent article of the present invention are described in detail below.

The fiber web preferably contains at least hydrophilic fibers. Any hydrophilic fibers can be used with no particular limitation provided that the fibers have a hydrophilic surface and are capable of forming a fiber web in which the individual fibers are not restricted by each other. Specific but non-limiting examples of such hydrophilic fibers include natural cellulose fibers such as wood pulp, for example, softwood pulp and hardwood pulp, cotton pulp, and straw pulp; regenerated cellulose fibers such as rayon and cuprammonium rayon; synthetic hydrophilic fibers such as polyvinyl alcohol fiber; and synthetic fibers having been rendered hydrophilic such as polyethylene fiber or polypropylene fiber having been rendered hydrophilic by treatment with a surface active agent. These hydrophilic fibers can be used either individually or as a combination of two or more thereof.

Of the above-described hydrophilic fibers preferred are cellulose fibers, in particular, bulky cellulose fibers, such as natural cellulose fibers and regenerated cellulose fibers. From an economical consideration, wood pulp, especially softwood kraft pulp is preferred. The bulky cellulose fibers are preferably used in an amount of at least 30 parts by weight, still preferably 50 to 99 parts by weight, per 100 parts by weight of the fiber web.

Preferred bulky cellulose fibers are cellulose fibers having a degree of fiber roughness of 0.3 mg/m or more. Cellulose fibers having a degree of fiber roughness of 0.3 mg/m or more are preferred because they are accumulated in a bulky state to form a bulky network structure, in which a superabsorbent polymer can be dispersed efficiently therethrough. The absorptivity of the superabsorbent polymer can thus be manifested more effectively, making further reductions in thickness possible. As a result, the bending stiffness of the absorbent member can be reduced to provide improved comfort. A preferred degree of fiber roughness is 0.3 to 2 mg/m, and a still preferred degree of fiber roughness is 0.32 to 1 mg/m. The terminology "degree of fiber roughness" as used herein means a measure indicative of the diameter of fibers having different degrees of diameter such as wood pulp fibers. The degree of fiber roughness can be measured, for example, with a fiber roughness meter "FS-200" manufactured by KAJANNI ELECTRONICS, LTD.

Other preferred bulky cellulose fibers are cellulose fibers whose cross section has a degree of fiber roundness of 0.5 to 1, particularly 0.55 to 1. Cellulose fibers having a degree of fiber roundness of 0.5 to 1 have a low resistance against liquid transfer and this have an increased rate of liquid permeation. The term "degree of fiber roundness" as used herein means the degree of circularity of the cross-section of a fiber, and the measurement of the degree of fiber roundness is described in the Examples hereinafter described.

Still other preferred bulky cellulose fibers are crosslinked cellulose fibers obtained by intramolecular and/or intermolecular crosslinking of cellulose fibers. Such crosslinked cellulose fibers are preferred for maintaining bulky structure even while wet. The crosslinked cellulose fibers are preferably crosslinked pulp obtained by crosslinking pulp fibers having an average fiber length of 2 to 5 mm.

In using the bulky cellulose fibers, it is preferable to appropriately combine the above-described attributes, i.e., degree of fiber roughness of 0.3 mg/m or more, intramolecular and/or intermolecular crosslinking, and degree of fiber roundness of 0.5 to 1.

It is preferable that the fiber web also contains thermally-fusible bonding fibers. Addition of thermally-fusible bonding fibers increases the compressive modulus of the absorbent sheet (liquid retentive absorbent member). The fiber web containing thermally-fusible bonding fibers retains its structure stably even when the absorbent sheet is wet.

Fibers which melt upon heating or subjecting to hot water to bond to each other can usually be used as thermally-fusible bonding fibers. Examples of thermally-fusible bonding fibers include polyolefin fibers such as polyethylene fiber and polypropylene fiber, polyvinyl alcohol fiber, polyester fibers, polyethylene-polypropylene conjugate fibers, polyethylene-polyester conjugate fibers, low-melting polyester-polyester conjugate fibers, polyvinyl alcohol-polypropylene conjugate fibers having a hydrophilic surface, and polyvinyl alcohol-polyester conjugate fibers. The thermally-fusible bonding fibers preferably have a fiber length of 2 to 60 mm and a fiber diameter of 0.1 to 3 deniers.

The fiber web preferably contains a reinforcing agent such as a polyamine-epichlorohydrin resin, dialdehyde starch, sponge, and carboxymethyl cellulose.

While the formulation of these fibers in the fiber web is not particularly limited, it is preferable that the fiber web contains 30 to 100 parts by weight of the hydrophilic fiber, 0 to 50 parts by weight of other fibers, and 0 to 30 parts by weight of the reinforcing agent, per 100 parts by weight of the fiber web. It is still preferable that the fiber web contains 50 to 100 parts by weight of the hydrophilic fiber, 0 to 20 parts by weight of other fibers, and 0 to 20 parts by weight of the reinforcing agent.

The fiber aggregate 15 having the absorbent surface 12 of the absorbent sheet 10 will now be illustrated.

The fiber aggregate 15 does not contain the superabsorbent polymer 16 on the side of the absorbent surface 12. The language "does not contain the superabsorbent polymer" as used herein does not mean that the fiber aggregate contains no superabsorbent polymer at all on the side of the absorbent surface 12, but means that the fiber aggregate contains substantially no superabsorbent polymer on the side of the absorbent surface 12 although existence of a trace amount of superabsorbent polymer which is inevitably accompanied by the preferred process for producing the absorbent sheet hereinafter described is permitted.

The fiber aggregate can be obtained through mechanical or physical entanglement, thermal bonding, and the like, of the fibers, and can include paper and nonwoven fabrics. Paper to be used as the fiber aggregate can be paper prepared by a wet paper making process or crepe paper. Nonwoven fabric to be used includes a nonwoven fabric prepared by carding, spunbonded fabric, melt blown fabric, and spunlaced fabric. As to the type of the fiber, the same fibers as used in the fiber web can be used for the fiber aggregate.

The superabsorbent polymer will now be described below.

As shown in FIG. 1, the superabsorbent polymer 16 is preferably present in the inside of the absorbent sheet 10 and dispersed in the spaces among the fibers constituting the absorbent sheet 10. In a still preferred mode, the superabsorbent polymer 16 is present in the inside of the fiber web 18 and dispersed in the spaces formed among the fibers constituting the fiber web 18 and the interface between the fiber web 18 and the fiber aggregate 15 as shown in FIG. 2. Such being the case, the superabsorbent polymer 16 is surely fixed in the absorbent sheet and prevented from causing gel blocking (Gel blocking is a phenomenon in which the swelled (gelled) superabsorbent polymer particles prevent water from permeating through the polymer particles). The language "the superabsorbent polymer is present in the inside of the absorbent sheet" as used herein does not mean that the superabsorbent polymer is not present at all on the surface of the absorbent sheet, but means that the most of the superabsorbent polymer is present in the inside of the absorbent sheet although existence of a trace amount of superabsorbent polymer which is present on the surface of the absorbent sheet and is inevitably accompanied by the preferred process for producing the absorbent sheet hereinafter described is permitted.

The superabsorbent polymer 16 is adhered to the fibers constituting the absorbent sheet 10, preferably the fibers constituting the fiber web 18. Therefore, the superabsorbent polymer 16 is fixed more firmly and surely prevented from causing gel blocking. Not all of the particles of the superabsorbent polymer 16 need to be adhered to the fibers. It is preferable, however, that at least 50% by weight, particularly 70% by weight or more, of the superabsorbent polymer 16 is adhered to the fibers.

Preferably, the superabsorbent polymer 16 is not dispersed two-dimensionally but three-dimensionally in the absorbent sheet as shown in FIG. 1 so that a large quantity of the superabsorbent polymer 16 may be dispersed. That is, the amount of a superabsorbent polymer that is spread and held two-dimensionally as in a conventional absorbent sheet is usually about 50 to 100 $g/m^2$ at the most. In the absorbent sheet 10, since the superabsorbent polymer 16 can be dispersed three-dimensionally, the maximum amount of the superabsorbent polymer 16 that can be spread can be increased up to about 200 to 300 $g/m^2$, which amount is almost three times that of a conventional absorbent sheet. The absorbent sheet 10 therefore has greatly increased liquid absorption. Additionally, the inherent absorbing performance of the superabsorbent polymer 16 becomes more effective due to the three-dimensional spread. That is, with the amount of the superabsorbent polymer 16 being equal to that used in a conventional absorbent sheet, the above-described absorbent sheet exhibits improved absorption and may have its thickness extremely reduced as compared with a conventional absorbent sheet.

The superabsorbent polymer is preferably spread in an amount of 1 to 300 $g/m^2$, still preferably 10 to 200 $g/m^2$, particularly preferably 20 to 150 $g/m^2$. If the amount is less than 1 $g/m^2$, the absorptivity is insufficient. If it exceeds 300 $g/m^2$, the strength between the fiber web and the fiber aggregate is reduced, and the superabsorbent polymer is liable to fall off. It is therefore recommended that the amount of the superabsorbent polymer to be spread falls within the above range.

The superabsorbent polymer is preferably one that can absorb and retain 20 or more times as much liquid as its own weight and is capable of gelling upon absorption. Such superabsorbent polymers include starch, crosslinked carboxymethyl cellulose, and polymers or copolymers of acrylic acid or an alkali metal salt thereof.

In the absorbent sheet it is preferable that the fiber aggregate has a basis weight of 10 to 200 $g/m^2$, the amount of the spread superabsorbent polymer is 1 to 300 $g/m^2$, and the fiber web has a basis weight of 10 to 200 $g/m^2$. It is still preferable that the fiber aggregate has a basis weight of 10 to 100 $g/m^2$, the amount of the spread superabsorbent polymer is 5 to 200 $g/m^2$, and the fiber web has a basis weight of 10 to 100 $g/m^2$.

The above-described absorbent sheet is preferably produced by a process which comprises the steps of:
spreading a superabsorbent polymer over a wet fiber web containing at least hydrophilic fibers and thermally-fusible bonding fibers,
overlaying a fiber aggregate on the fiber web, and
drying the combination of the fiber web and the fiber aggregate to form a unitary body.

In more detail, a fiber web containing hydrophilic fibers is formed. The method for forming the fiber web is not particularly restricted. Either a dry paper making process or a wet paper making process can be used, with the latter being preferred.

In carrying out wet paper making for preparing a fiber web, fiber webforming fibers and components, preferably the above-described hydrophilic fibers, thermally-fusible bonding fibers and reinforcing agent, etc., are dispersed in water in prescribed concentrations to prepare a slurry. The concentrations of the hydrophilic fibers, thermally-fusible bonding fibers, and reinforcing agent in the slurry may be selected from those used in a general wet paper making process. The relative proportions of the hydrophilic fiber, thermally-fusible bonding fiber, and reinforcing agent, etc. are selected so that the resulting fiber web may have the above-mentioned composition.

Over the thus obtained fiber web is spread the aforesaid superabsorbent polymer while the fiber web is wet. The fiber web preferably has such wetness that it contains about 20 to 500 parts by weight, still preferably 50 to 300 parts by weight, of water per 100 parts by weight of the fiber web on a dry basis. If the water content is less than 20 parts by weight, the spread superabsorbent polymer cannot absorb sufficient water to swell and to acquire stickiness, tending to be fixed unsuccessfully. If the water content exceeds 500 parts by weight, the superabsorbent polymer absorbs excessive water and tends to fail to dry up in the drying step hereinafter described. Accordingly, the water content of the wet fiber web preferably falls within the above range.

The superabsorbent polymer is spread over the wet fiber web, whereby the superabsorbent polymer absorbs water, assumes stickiness, and is embedded into the fibers constituting the fiber web, and adhered and fixed to the fibers. Since the fibers constituting the wet fiber web are not yet bound to each other and not yet restricted, the superabsorbent polymer can be dispersed therein three-dimensionally. Accordingly, a larger amount of a superabsorbent polymer can be stably fixed than in conventional absorbent sheets. The superabsorbent polymer may be spread uniformly all over the wet fiber web or, if desired, may be spread in parallel stripes at certain intervals along the longitudinal direction or may be spread intermittently in the longitudinal direction of the fiber web.

Then, the above-described fiber aggregate is put on the fiber web with the superabsorbent polymer spread thereon. Since the fibers in the fiber web is not yet restricted at this point in time, the superabsorbent polymer are embedded deeper into the fiber web, and the fibers of the fiber web and those of the fiber aggregate are easily entangled with each other.

The combination of the fiber web and the fiber aggregate is dried subsequently, whereupon the fibers are entangled with each other. As a result of this entanglement combined with hydrogen bonds and thermal bonding, the fiber web and the fiber aggregate are integrated into a unitary body, and the superabsorbent polymer adhered to the fibers are dried and fixed to thereby provide the above-described absorbent sheet. The drying temperature preferably ranges from 100° to 180° C., still preferably from 105° to 150° C., while varying depending on the type of the fibers used. Through this step, the fiber web and the fiber aggregate are integrated into a unitary body, and the fibers constituting the fiber web are bound to each other. As a result, the absorbent sheet is formed. The drying means is not particularly limited and includes, for example, a Yankee dryer and an air-through dryer.

Usual paper making machines, such as a wire paper making machine and a cylinder paper making machine, can be used for preparing the absorbent sheet. As for other steps than the above, steps generally used in paper making process can be adopted appropriately.

The absorbent article of the present invention is not limited to the preferred embodiments which are explained in detail hereinabove. A variety of variations of said embodiments can exist without departing the scope of the present invention. For example, any absorbent member which satisfies both of the specific ranges of the bending stiffness and the compressive modulus, can be used for the absorbent article of the present invention without limitation to the absorbent member shown in FIG. 1 and FIG. 2.

EXAMPLES

The present invention will now be illustrated in greater detail by way of Examples and Comparative Examples, but it should be understood that the present invention is not construed as being limited thereto. Unless otherwise specified, all the parts are by weight.

PREPARATION EXAMPLE 1

Preparation of Absorbent Sheet

Eighty parts of crosslinked pulp having a degree of fiber roughness of 0.32 mg/m and a degree of fiber roundness of 0.30 (HIGH BULK Additive (trade name) produced by Weyerhaeuser Co., Ltd.) and 20 parts of low-melting polyester bonding fibers having a fineness of 1.1 deniers and a fiber length of 7 mm (TM-07N (trade name) produced by Teijin Ltd.) were mixed and dispersed in 20 parts of water in a prescribed concentration. The resulting dispersion was formed into a fiber web having a dry basis weight of 40 g/m$^2$ in a forming portion of a wet paper making machine. The fiber web was dehydrated by a suction box and a press portion to reduce the water content to 100 parts per 100 parts of the web on a dry basis. After passing through the press portion, a superabsorbent polymer (CAW-4S (trade name) produced by Nippon Shokubai Kagaku Kogyo Co., Ltd.) was spread uniformly over the dehydrated but still wet fiber web in an amount of 80 g/m$^2$.

On the superabsorbent polymer-spread side of the fiber web was overlaid absorbent paper having the same composition as the fiber web (basis weight: 40 g/m$^2$) which had been previously prepared. The combination of the fiber web and absorbent paper was led to a dryer, where it was dried at 130° C. and formed into a unitary body, thereby to obtain a unitary absorbent sheet having fixed therein the superabsorbent polymer. The resulting absorbent sheet is designated as absorbent sheet A.

The degree of fiber roughness and the degree of fiber roundness of the chemical pulp used in the above absorbent sheet were measured as follows.

Measurement of Degree of Fiber Roughness

Measurement was made with a fiber roughness meter FS-200 manufactured by KAJANNI ELECTRONICS Ltd.

In order to measure the true weight of the chemical pulp, the chemical pulp was dried in a vacuum dryer at 100° C. for 1 hour to remove water which exists in the chemical pulp. Immediately thereafter, about 1 g of the chemical pulp was weighed out to a precision of ±0.1 mg and completely disaggregated in 150 ml of water by means of a mixer attached to the fiber roughness meter taking care not to damage the chemical pulp. The resulting suspension was diluted with water to make the volume of the suspension 5000 ml. A 50 ml aliquot of the diluted suspension was precisely measured out as a sample solution for measurement of fiber roughness. The degree of fiber roughness was determined according to the operating procedure of the fiber roughness meter.

Measurement of Degree of Fiber Roundness

The chemical pulp was transversely sliced with care not to change the cross-sectional area, and an electron micrograph of the section was taken. The micrograph was analyzed by an image analyzer (Avio EXCEL (trade name) manufactured by Nippon Avionics Co., Ltd.) to obtain a degree of fiber roundness according to the following formula. Measurement was made on arbitrarily chosen 100 points to obtain the average.

Degree of fiber roundness=4×π×(cross-sectional area of a fiber)/(circumference of the cross-section of the fiber)$^2$

PREPARATION EXAMPLE 2

Preparation of Absorbent Sheet

An absorbent sheet was prepared in the same manner as in Preparation Example 1, except for changing the dry basis weight of the fiber web and the fiber aggregate each to 30 g/m$^2$. The resulting absorbent sheet is designated absorbent sheet B.

PREPARATION EXAMPLE 3

Preparation of Absorbent Sheet

An absorbent sheet was prepared in the same manner as in Preparation Example 1, except for using 97 parts of crosslinked pulp having a degree of fiber roughness of 0.32 mg/m and a degree of fiber roundness of 0.30 (HIGH BULK additive (trade name) produced by Weyerhaeuser Co., Ltd.) and 3 parts of polyvinyl alcohol fiber having a fineness of 1 denier and a fiber length of 3 mm (Fibribond (trade name) produced by Sansho K. K.). The resulting absorbent sheet is designated absorbent sheet C.

PREPARATION EXAMPLE 4

Preparation of Absorbent Sheet

Mercerized pulp having a degree of fiber roughness of 0.36 mg/m and a degree of fiber roundness of 0.80 (POROSANIER-J (trade name) produced by ITT Rayonier Inc.), a hydrophilic cellulose fine fiber having an average fiber length of 0.12 mm which was obtained by hydrolyzing carefully refined pulp, washing with water, drying, and mechanically grinding into fine fibers (KC Flock W-100 (trade name) produced by Sanyo-Kokusaku Pulp Co., Ltd.), and polyvinyl alcohol fiber having a fineness of 1 denier and a fiber length of 3 mm (Fibribond (trade name) produced by Sansho K. K.) were uniformly dispersed in water in a concentration of 0.16 wt %, 0.03 wt %, and 0.01 wt %, respectively, to prepare an aqueous slurry having total pulp and fiber content of 0.20 wt %. The slurry was spread over the wire having a mesh size of 90 μm (166 mesh) of a paper making machine to form a paper layer on the wire. The paper layer was dehydrated and dried by a suction box at a rate of 6 ml/cm$^2$ sec and dried in a dryer to obtain absorbent paper having a basis weight of 30 g/m$^2$. The resulting absorbent paper contained 80 parts of the mercerized pulp, 15 parts of the hydrophilic fine fiber, and 5 parts of the polyvinyl alcohol fiber per 100 parts of the absorbent paper.

The absorbent paper was cut to a length of 175 mm and a width of 145 mm, and a hot-melt adhesive P-618B (trade name, produced by Toyo Patro Light) was spirally applied to the central 80 mm wide area over the length of the absorbent paper at a spread of 10 g/m². A superabsorbent polymer (CAW-4S (trade name) produced by Nippon Shokubai Kagaku Kogyo Co., Ltd.) was then spread uniformly on the central 60 mm wide area over the length of the absorbent paper in an amount of 80 g/m². Both sides of the absorbent paper (the areas where no hot-melt adhesive were applied) were folded back to obtain an absorbent sheet with the superabsorbent polymer being fixed inside. The resulting absorbent sheet is designated absorbent sheet D.

COMPARATIVE PREPARATION EXAMPLE 1

Fluff pulp obtained by fibrillating a pulp sheet with a hammer mill (NB-420 (trade name) produced by Weyerhaeuser Co., Ltd.) was accumulated to a basis weight of 400 g/m², and a superabsorbent polymer (CAW-4S (trade name) produced by Nihon Shokubai Kagaku Kogyo Co., Ltd.) was spread uniformly on a 60 mm wide and 165 mm long area in an amount of 80 g/m². Wet processed absorbent paper (70 mm wide, 175 mm long) having a basis weight of 18 g/m² which comprised soft wood kraft pulp having a degree of fiber roughness of 0.18 mg/m and a degree of fiber roundness of 0.32 (SKEENA PRIME (trade name) produced by Skeena Cellulose Co.) was overlaid thereon. The combination of the fluff pulp and the absorbent paper was compressed to a thickness of 7 mm to prepare an absorbent sheet. The resulting absorbent sheet is designated absorbent sheet E.

COMPARATIVE PREPARATION EXAMPLE 2

An absorbent sheet was prepared in the same manner as in Comparative Preparation Example 1, except that the combination was compressed to a thickness of 4 mm. The resulting absorbent sheet is designated absorbent sheet F.

COMPARATIVE PREPARATION EXAMPLE 3

An absorbent sheet was prepared in the same manner as in Comparative Preparation Example 1, except that the fluff pulp was accumulated to a basis weight of 200 g/m² and the combination was compressed to a thickness of 2 mm. The resulting absorbent sheet is designated absorbent sheet G.

COMPARATIVE PREPARATION EXAMPLE 4

An absorbent sheet was prepared in the same manner as in Preparation Example 4, except for using absorbent paper having a basis weight of 30 g/m² which was previously prepared from soft wood pulp having a degree of fiber roughness of 0.18 mg/m and a degree of fiber roundness of 0.32 (SKEENA PRIME (trade name) produced by Skeena Cellulose Co.). The resulting absorbent sheet is designated absorbent sheet H.

Absorbent sheets A to H were tested in accordance with the following test methods. The results obtained are shown in Table 1 below.

Thickness

The absorbent sheet was cut to an appropriate size. A disk of 17.8 mm in diameter (load area: 10 cm²) was put thereon to apply a load of 2.5 g/cm², and the thickness of the sheet under the load was measured. Measurement was made on 10 points per sample to obtain an average thickness.

Bending Stiffness

A 70 mm long and 30 mm wide test piece was cut out of the absorbent sheet with its longitudinal direction agreeing with the longitudinal direction of an absorbent article. The test piece was clamped by chucks at a 1 cm distance and bent at a constant rate of deformation of 0.50 (cm$^{-1}$)/sec within a range of a curvature (K) of from −2.5 to +2.5 (cm$^{-1}$) by use of a bend tester manufactured by Kato Tec. To minimize the influence of gravity, the test piece was held vertically.

A bending stiffness (B) per unit area, which was a slope of the M-K curve of bending moment(M) per unit length of the test piece vs. curvature (K), was obtained.

The slope between K=0.5 and 1.5 (front bend) and the slope between K=−0.5 to −1.5 (back bend), taken as Bf and Bb, respectively, were measured from the characteristics of the increase of the absolute value of K, and the average of Bf and Bb was taken as a bending stiffness (B).

B=(Bf+Bb)/2

Bf: B in front bend

Bb: B in back bend

Compressive Modulus

Figure 7:
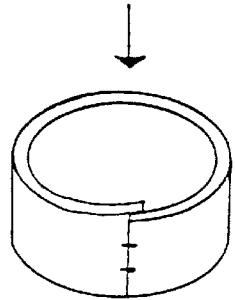
FIG. 7 schematically illustrates the manner of measurement for a compressive modulus.

A 170 mm long and 40 mm wide test piece was cut out of the absorbent sheet with its longitudinal direction agreeing with the longitudinal direction of an absorbent article. The test piece was made into a cylindrical shape as shown in FIG. 7, with the ends overlapping in a width of 2 mm, and the overlap was stapled at two points. The cylinder put vertically was compressed by applying a load of 5 kg on the top of the cylinder at a rate of 10 mm/min with Tensilon manufactured by Orientec. The slope of the curve of deformation (ΔL) vs. load (F), i.e., F/ΔL, was obtained. The compressive modulus E is obtained from the F/ΔL, the area (A) calculated from the thickness and length of the absorbent sheet, and the initial height of the cylinder (L) according to the following formula:

TABLE 1

$E = (F/\Delta L) \cdot (L/A)$ [dyne/cm²]

|  |  | Absorbent Sheet | Thickness of Absorbent Sheet (mm) | Bending Stiffness (gf · cm) | Compressive Modulus (dyne/cm²) |
|---|---|---|---|---|---|
| Preparation Examples | 1 | A | 1.0 | 0.40 | 7.5 × 10⁶ |
|  | 2 | B | 0.8 | 0.20 | 6.0 × 10⁶ |
|  | 3 | C | 0.9 | 0.40 | 18 × 10⁶ |
|  | 4 | D | 1.0 | 0.60 | 26 × 10⁶ |
| Comparative Preparation Examples | 1 | E | 7.0 | 3.35 | 0.038 × 10⁶ |
|  | 2 | F | 4.0 | 1.27 | 0.2 × 10⁶ |
|  | 3 | G | 2.0 | 0.30 | 0.1 × 10⁶ |
|  | 4 | H | 1.5 | 0.07 | 0.077 × 10⁶ |

EXAMPLE 1

A sanitary napkin having the structure shown in FIG. 3 was prepared.

A 140 mm wide film of low-density polyethylene having a basis weight of 25 g/m² was used as a liquid impermeable antileakage layer 3. Absorbent sheet A cut to a length of 170 mm and a width of 73 mm was used as an absorbent member 2. The both sides and the back surface of the absorbent member 2 were covered with the antileakage layer 3 in such a manner that the antileakage layer 3 covering the back surface of the absorbent member 2 gave a width of 95 mm. The absorbent member 2 was fixed to the antileakage layer 3 with a fixing agent 6.

A surface layer 1 having a width of 100 mm was put over the upper side of the combination of the absorbent member 2 and the antileakage layer 3, and the surface layer 1 and the antileakage layer 3 at both sides were heat-sealed and trimmed to obtain a sanitary napkin having a width of 85 mm. Two hot melt adhesive strips each having a basis weight of 30 g/m$^2$, a width of 20 mm, and a length of 115 mm were provided on the back side of the sanitary napkin (the side opposite to the surface layer 1).

The surface layer 1 used was a perforated polyethylene film obtained by making perforations having a diameter of 0.5 mm in a polyethylene film having a basis weight of 30 g/m$^2$. The perforation ratio of the antileakage layer was 20%.

EXAMPLES 2 TO 4

Sanitary napkins having the structure shown in FIG. 3 were obtained in the same manner as in Example 1, except for replacing absorbent sheet A with absorbent sheets B to D.

EXAMPLE 5

A sanitary napkin having the structure shown in FIG. 4 was prepared in the same manner as in Example 1, except that the absorbent member had a narrowed portion having a width of 60 mm. The narrowed portion was positioned at 75 mm from the front end of the absorbent member. The narrowed portion of the sanitary napkin corresponding to the narrowed portion of the absorbent member had a width of 75 mm.

COMPARATIVE EXAMPLES 1 TO 4

Sanitary napkins having the structure shown in FIG. 3 were prepared in the same manner as in Example 1, except for replacing absorbent sheet A with absorbents sheets E to H.

COMPARATIVE EXAMPLE 5

A sanitary napkin having the structure shown in FIG. 4 was prepared in the same manner as in Example 5, except for replacing absorbent sheet A with absorbents sheet G.

The following tests were performed on the sanitary napkins obtained in Examples and Comparative Examples in order to evaluate the influences of the bending stiffness and compressive modulus of the absorbent member on the comfort of the sanitary napkin as worn. The results obtained are shown in Table 2 below.

1) Foreign feeling of Sanitary Napkin While Worn

A foreign feeling of the sanitary napkin while worn was organoleptically evaluated according to the following standard.

A . . . No foreign feeling was felt at the crotch at all.

B . . . Almost no foreign feeling was felt at the crotch.

C . . . Stiffness or a foreign feeling were slightly felt at the crotch.

D . . . Stiffness or a foreign feeling were felt at the crotch.

2) Deformation

Figure 8:
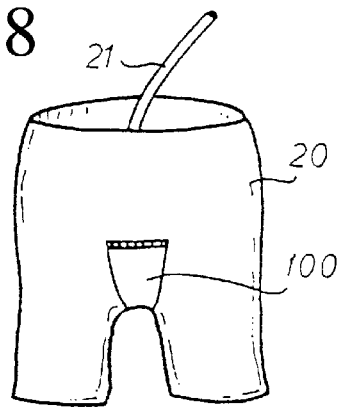
FIG. 8 schematically illustrates a movable model of female hips applied with a sanitary napkin to the crotch.

Each of the sanitary napkins obtained in the Examples and Comparative Examples was applied to a movable model 20 of female hips as shown in FIG. 8. After fitting panties to the model 20, the model was made to take a walking movement at a rate of 100 steps/min (corresponding to a walking speed of 50 m/min).

While keeping the model 70 in a moving mode, 5 g of defibrinated horse blood was poured into the sanitary napkin through a tube 21, and the walking movement was continued for 20 minutes at the same walking speed (5 g-absorption). After the 20 minute walking, the deformation of the napkin was evaluated in terms of rate of deformation in the lateral direction of the sanitary napkin at the center of the crotch portion of the panties.

A .. . Almost not deformed (rate of deformation in the lateral direction: 25% or less).

B . . . Slightly deformed (rate of deformation in the lateral direction: 25 to 35%).

C . . . Deformed (rate of deformation in the lateral direction: more than 35%).

The rate of deformation in the lateral direction was calculated according to the following equation:

$$\text{Rate of deformation in lateral direction} = [(L_0-1)/L_0] \times 100 \ (\%)$$

L: lateral length of the napkin after the test.

$L_0$: lateral length of the napkin before the test.

3) Leak Test (Number of Leaks)

Each of the sanitary napkins 100 obtained in Examples and Comparative Examples was applied to the movable model 20 of female hips as shown in FIG. 8, and panties were fitted thereon. The model 20 was made to take a walking movement at a rate of 100 steps/min (corresponding to a walking speed of 50 m/min).

While keeping the model 20 in a moving mode, 5 g of defibrinated horse blood was poured into the sanitary napkin through the tube 21, and the walking movement was continued for 20 minutes at the same walking speed (5 g-absorption). Another 5 g of defibrinated horse blood was again poured, followed by walking at the same speed for another 20 minutes (10 g-absorption). The test was conducted 10 times per sample, and the samples occurred a leak at 5 g-absorption and 10 g-absorption were counted.

TABLE 2

| | Absorbent Sheet | Shape of Napkin | Thickness of Napkin (mm) | Foreign Feeling | Deformation | Number of Leaks 5 g | 10 g |
|---|---|---|---|---|---|---|---|
| Examples | | | | | | | |
| 1 | A | Rectangular | 1.5 | B | A~B | 0 | 2 |
| 2 | B | Rectangular | 1.3 | B | A~B | 0 | 2 |
| 3 | C | Rectangular | 1.3 | B | A | 0 | 1 |
| 4 | D | Rectangular | 1.5 | B | A | 0 | 2 |
| 5 | A | Narrowed | 1.5 | A | A | 0 | 0 |

TABLE 2-continued

|  | Absorbent Sheet | Shape of Napkin | Thickness of Napkin (mm) | Foreign Feeling | Deformation | Number of Leaks 5 g | 10 g |
|---|---|---|---|---|---|---|---|
| Comparative Examples |  |  |  |  |  |  |  |
| 1 | E | Rectangular | 7.5 | D | C | 3 | 10 |
| 2 | F | Rectangular | 4.5 | C | B~C | 1 | 5 |
| 3 | G | Rectangular | 2.5 | B | B~C | 1 | 5 |
| 4 | H | Rectangular | 2.0 | A | C | 7 | 10 |
| 5 | G | Narrowed | 2.5 | B | B | 0 | 3 |

As is apparent from the results shown in Table 2 above, the sanitary napkin using an absorbent member having a specific bending stiffness and a specific compressive modulus, when applied to the body, shows small repulsion in its lateral direction under compression at the crotch and has a small bending stiffness so that a foreign feeling is hardly felt. Further, because of its high compressive modulus, the sanitary napkin is hardly deformed. Therefore, it can be understood that there is provided an absorbent article of a simple structure which gives improved comfort while worn as a sanitary napkin, exhibits high liquid absorption, and hardly causes leaks.

What is claimed is:

1. An absorbent article comprising:

a liquid retentive absorbent member and a liquid impermeable anti-leakage layer, said liquid retentive absorbent member has a bending stiffness of 0.05 to 1.0 gf·cm along its lateral direction, the bending stiffness being measured by bending the absorbent article in the lateral direction, and a compressive modulus of $2 \times 10^6$ to $1 \times 10^8$ dyne/cm$^2$ along the lateral direction, the compressive modulus being measured by making the absorbent member into a cylindrical shape and compressing the cylindrical shape in a height direction, whereby said absorbent article is comfortable to a wearer while being substantially resistant to deformation and leakage.

2. The absorbent article according to claim 1, wherein said liquid retentive absorbent member includes at least a superabsorbent polymer and an absorbent sheet, said absorbent sheet being made up of at least hydrophilic fibers and thermally-fusible bonding fibers.

3. The absorbent article according to claim 1, wherein said liquid retentive absorbent member has an absorbent sheet containing at least a superabsorbent polymer, said absorbent sheet has a fiber aggregate layer and a fiber web layer; and P1 means for bonding said fiber aggregate layer and said fiber web layer to form a unitary body, said fiber aggregate layer having an absorbent surface containing substantially no superabsorbent polymer on a side of said absorbent member; said fiber web layer includes at least one of hydrophilic fibers and thermally-fusible bonding fibers, said superabsorbent polymer being adhered to the fibers constituting said absorbent sheet and being dispersed and fixed predominantly in said fiber web layer and at the interface between said fiber web layer and said fiber aggregate layer.

4. The absorbent article according to claim 1, wherein said liquid retentive absorbent member has a thickness of 0.3 to 1.5 mm. under a load of 2.5 g/cm$^2$ to reduce and stabilize the bending stiffness.

5. The absorbent article according to claim 1, wherein said liquid retentive absorbent member has a shape of at least one of a crotch of a wearer, a disposable diaper, a nursing breast pad, and a rectangle.

6. The absorbent article according to claim 3, wherein said means for bonding includes at least of a mechanical entanglement of said fiber aggregate layers with said fiber web layer, hydrogen bonding with a reinforcing agent, and thermal bonding.

7. The absorbent article according to claim 3, wherein said fiber web layer includes at least one of a natural cellulose fibers, synthetic hydrophilic fibers, and a combination of natural cellulose fibers and synthetic hydrophilic fibers.

8. The absorbent article according to claim 3, wherein said fiber aggregate includes at least one of paper and nonwoven fabrics.

9. The absorbent article according to claim 3, wherein said superabsorbent polymer is substantially fixed to fibers of said fiber web and dispersed in spaces among said fibers of said fiber web to prevent gel blocking.

* * * * *